(12) United States Patent
Bednarz et al.

(10) Patent No.: US 7,951,941 B2
(45) Date of Patent: May 31, 2011

(54) PROCESS FOR PREPARING 5-ALKYL-7H-PYRROLO[2,3-D]PYRIMINDINE-2-OLS

(75) Inventors: Mark S. Bednarz, Yardley, PA (US); Ramanaiah C. Kanamarlapudi, Bridgewater, NJ (US); Wenxue Wu, Princeton Junction, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 855 days.

(21) Appl. No.: 11/876,051

(22) Filed: Oct. 22, 2007

(65) Prior Publication Data

US 2008/0097098 A1 Apr. 24, 2008

Related U.S. Application Data

(60) Provisional application No. 60/853,891, filed on Oct. 23, 2006.

(51) Int. Cl.
*C07D 487/04* (2006.01)
(52) U.S. Cl. ..................................................... 544/280
(58) Field of Classification Search .................. 544/280
See application file for complete search history.

(56) References Cited

FOREIGN PATENT DOCUMENTS

| EP | 0733633 | 9/1996 |
|---|---|---|
| WO | WO 2006/084996 | 8/2006 |

OTHER PUBLICATIONS

Vippagunta, S.R., (Adv. Drug. Delivery Rev., 2001, 48, pp. 3-26).*
Amarnath, V. and Madhav, R., *Synthesis*, 837 (1974).
Bookser, B.C., et al., *J. Med. Chem.* 48:7808-7820 (2005).
Choi, H.-S., et al. *Bioorg. Med. Chem. Lett.* 16:2689-2692 (2006).
Choi, H.-S., et at., *Bioorg. Med. Chem. Lett.* 16:2173-2176 (2006).
Foloppe, N., et al., *J. Med. Chem.* 48:4332-4345 (2005).
Gangjee, A., et al., *J. Med. Chem.* 49:1055-1065 (2006).
Girgis et al, *Synthesis* 101-104 (1985).
Kanamarlapudi, R.C. et al., *Org. Process Res. & Dev.* 11:86-89 (2007).
Kempson, J., et al., *Bioorg. Med. Chem. Lett.* 15:1829-1833 (2005).
Migawa, M.T. and Townsend, L.B., *J. Org. Chem.* 66:4776-4782 (2001).
Seela, F. and Peng, X., *J. Org. Chem.* 71:81-90 (2006).
Smalley, T. L., et al. *Bioorg. Med. Chem. Lett.* 16:2091-2094 (2006).
Traxler, P., et al., *Med. Res. Rev.* 21:499-512 (2001).
Wamhoff and Wehling, *Synthesis* 51 (1976).
West, *J. Org. Chem.* 26:4959 (1961).
International Search Report of Corresponding International Patent Application No. PCT/US2007/082049 date of mailing Oct. 22, 2007.

* cited by examiner

*Primary Examiner* — Susanna Moore
(74) *Attorney, Agent, or Firm* — Max Bachrach

(57) ABSTRACT

Methods of preparing 5-alkyl-7H-pyrrolo[2,3-d]pyrimidin-4-ols are described, as are novel compounds useful in their preparation. A specific method encompassed by the invention is represented in the following scheme:

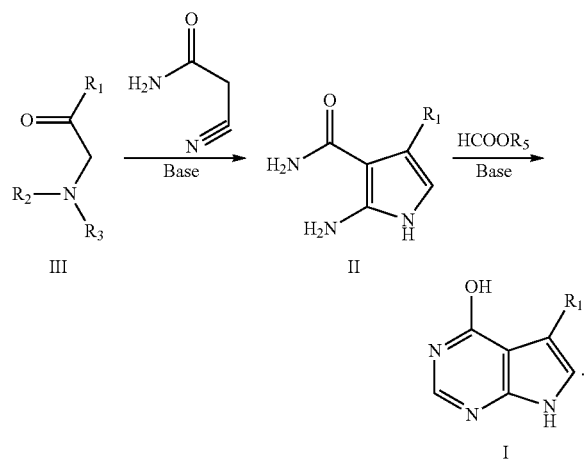

32 Claims, No Drawings

PROCESS FOR PREPARING 5-ALKYL-7H-PYRROLO[2,3-D] PYRIMINDINE-2-OLS

This application claims priority to U.S. provisional application No. 60/853,891, filed Oct. 23, 2006, the entirety of which is incorporated herein by reference.

1. FIELD OF THE INVENTION

This invention relates to methods of synthesizing 5-alkyl-7H-pyrrolo[2,3-d]pyrimidin-4-ols.

2. BACKGROUND

Pyrrolo[2,3-d]pyrimidines have attracted much interest because of their biological importance. See, e.g., Choi, H. -S., et al., *Bioorg. Med. Chem. Lett.* 16:2689-2692 (2006); Choi, H. -S., et al., *Bioorg. Med. Chem. Lett.* 16:2173-2176 (2006); Smalley, T. L., et al., *Bioorg. Med. Chem. Lett.* 16:2091-2094 (2006); Gangjee, A., et al., *J. Med. Chem.* 49:1055-1065 (2006); Seela, F. and Peng, X., *J. Org. Chem.* 71:81-90 (2006); Foloppe, N., et al., *J. Med. Chem.* 48:4332-4345 (2005); Kempson, J., et al., *Bioorg. Med. Chem. Lett.* 15:1829-1833 (2005); Traxler, Peter, et al., *Med. Res. Rev.* 21:499-512 (2001). Syntheses of pyrrolo[2,3-d]pyrimidines typically require the preparation of 5-alkyl-7H-pyrrolo[2,3-d]pyrimidin-4-ol intermediates. See, e.g., U.S. patent application Ser. No. 11/354,636, filed Feb. 15, 2006. But despite their importance, few methods are known for preparing 5-alkyl-7H-pyrrolo[2,3-d]pyrimidin-4-ols with wide applicability. See e.g., Amarnath and Madhav, *Synthesis*, 837 (1974).

Typical synthetic methods include a desulfurization step, as illustrated in Scheme 1:

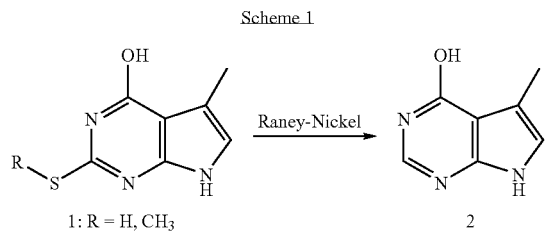

See, e.g., West, *J. Org. Chem.* 26:4959 (1961); Aono et al., EP 0733633-B1. Desulfurization is typically carried out using Raney Nickel in large excess, which can result in large amounts of heavy metal waste. In addition, when R is methyl, the process requires long heating times. See, e.g., U.S. patent application Ser. No. 11/354,636, filed Feb. 15, 2006. When R is hydrogen, the desulfurization is typically faster, but it requires multiple steps and provides lower yields.

5-Alkyl-7H-pyrrolo[2,3-d]pyrimidin-4-ols can also be prepared from the cyanopyrrole 3, as illustrated below in Scheme 2:

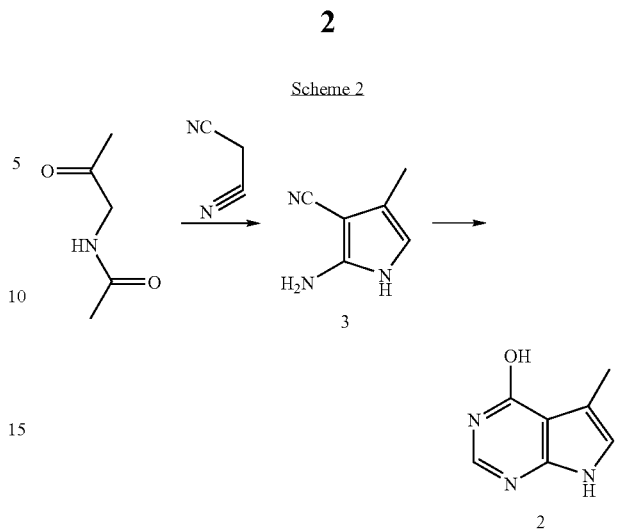

See e.g., Wamhoff and Wehling, *Synthesis* 51 (1976). Unfortunately, this reaction uses harsh conditions and provides poor yields. See also, Girgis et al., *Synthesis* 101 (1985). Consequently, new methods of preparing 5-alkyl-7H-pyrrolo [2,3-d]pyrimidin-4-ols are needed.

3. SUMMARY OF THE INVENTION

This invention is directed, in part, to novel methods of preparing 5-alkyl-7H-pyrrolo[2,3-d]pyrimidin-4-ols and salts and solvates thereof.

In one embodiment, a compound of formula I is prepared from a compound of formula II, as shown below:

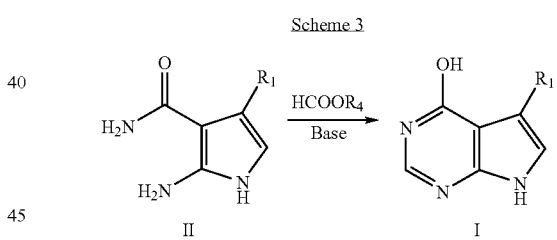

wherein the various substituents are defined herein. In a particular embodiment, the compound of formula II is prepared from a compound of formula III:

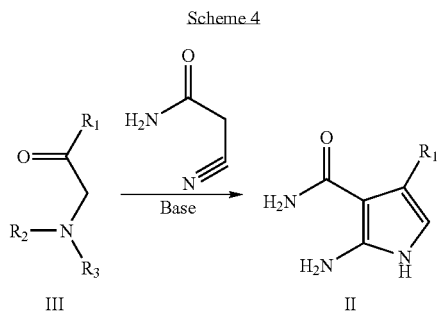

wherein the various substituents are defined herein.

Another embodiment encompasses compounds of formula II:

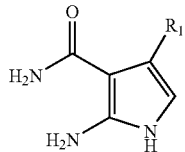

and salts and solvates thereof, wherein $R_1$ is defined herein.

4. DETAILED DESCRIPTION

This invention is directed, in part, to methods of preparing compounds of formula I:

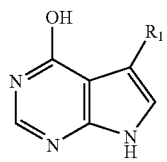

wherein $R_1$ is hydrogen or optionally substituted alkyl, aryl, heterocycle, arylalkyl, or heterocycloalkyl. It is well known that compounds of formula I can exist as tautomers:

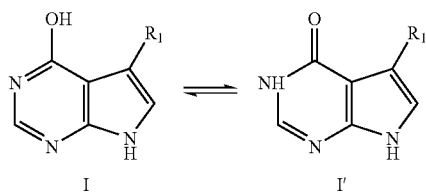

Formula I, as used herein, encompasses compounds of formulae I and I', and mixtures thereof.

4.1. Definitions

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "alkoxy" means an —O-alkyl group. Examples of alkoxy groups include —OCH$_3$, —OCH$_2$CH$_3$, —O(CH$_2$)$_2$CH$_3$, —O(CH$_2$)$_3$CH$_3$, —O(CH$_2$)$_4$—CH$_3$, and —O(CH$_2$)$_5$CH$_3$.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include, but are not limited to, anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include, but are not limited to, acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include, but are not limited to, benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

Unless otherwise indicated, the term "salts" includes pharmaceutically acceptable salts.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) and urea (—NH-CONH-alkyl-).

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alkyl, aryl, or heteroaryl" has the same meaning as "optionally substituted alkyl, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

4.2. Methods

This invention encompasses methods of preparing compounds of formula I:

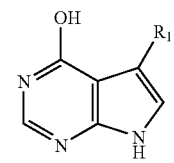

and salt and solvates thereof, wherein $R_1$ is hydrogen or optionally substituted alkyl, aryl, heterocycle, arylalkyl, or heterocycloalkyl.

In one embodiment, the compound of formula I is prepared by contacting a compound of formula II:

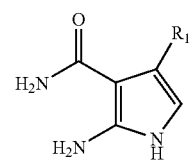

with a formic acid ester of formula $HCOOR_5$ under conditions sufficient to provide the compound of formula I, wherein $R_5$ is optionally substituted alkyl, aryl, or arylalkyl.

Conditions sufficient to provide the compound of formula I include a base catalyst in a solvent. Suitable bases include those with conjugate acids possessing $pK_a$s greater than 12, and mixtures thereof. Examples of bases include metal hydroxides (e.g., lithium hydroxide, sodium hydroxide, potassium hydroxide), metal alkoxides (e.g., lithium methoxide, sodium methoxide, sodium ethoxide), and metal amides (e.g., lithium hexamethyldisilazide). Suitable solvents include alcohols (e.g., methanol, ethanol), amides (e.g., dimethylformamide, dimethylacetamide, N-methylpyrrolidone), ethers (e.g., tetrahydrofuran, dioxane, dimethoxyethane), and nitriles (e.g., acetonitrile).

Any suitable amount of solvent may be used. In one embodiment, the amount is from about 1 to about 50, about 5 to about 30, or about 10 to about 25 times the weight amounts of the starting compound. Similarly, the any suitable amount of base may be used. In one embodiment, the amount is from about 1 to about 10, about 1 to about 5, or about 1 to about 3 molar equivalents of the starting compound.

The compound of formula II may be dissolved, dispersed, suspended or otherwise suitably distributed in the solvent. In a particular method, the formic acid ester is added to the solution, followed by the addition of the base. Addition of the base can occur at any suitable temperature, including temperatures from about 0° C. to about 80° C., about 20° C. to about 80° C., and about 40° C. to about 60° C., and can occur over any suitable duration, including periods of from about 0.25 to about 5 hours, about 0.25 to about 3 hours, and about 0.25 to about 2 hours. In certain methods, the mixture is stirred or otherwise mixed to facilitate the reaction. In certain methods, the reaction is conducted at a temperature of from about 20° C. to about 100° C., about 40° C. to about 80° C., or about 50° C. to about 70° C., and for a time of from about 0.5 to about 20 hours, about 1 to about 10 hours, or from about 2 to about 8 hours. Completion of the reaction can be determined by any suitable analytical method.

In a particular method, esters remaining at the completion of the reaction are hydrolyzed, the organic solvent(s) is/are removed, and the pH of the reaction mixture is adjusted to precipitate the product. In a certain method, the pH is from about 2 to about 10, from about 4 to about 10, or from about 4 to about 8. In preferred methods, the product of formula I is isolated with good yield (e.g., greater than about 30 or 50 percent) and high purity (e.g., greater than about 90 or 98 percent as determined by HPLC).

The compound of formula II may be prepared by contacting a compound of formula III:

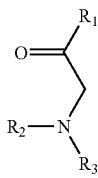

with cyanoacetamide under conditions sufficient to provide the compound of formula II, wherein $R_2$ and $R_3$ are each independently hydrogen or $R_4CO-$, or are taken together with the nitrogen atom to which they are attached to provide a heterocycle (e.g., phthalimido, succinimido); and $R_4$ is optionally substituted alkyl, aryl, arylalkyl, alkoxy, or aryloxy. Compounds of formula III are commercially available, or can be prepared by methods known in the art.

Conditions sufficient to provide the compound of formula II include a base catalyst in a solvent. Suitable bases include those with conjugate acids possessing $pK_a$s greater than 12, and mixtures thereof. Examples of bases include metal hydroxides (e.g., lithium hydroxide, sodium hydroxide, potassium hydroxide), metal alkoxides (e.g., lithium methoxide, sodium methoxide, sodium ethoxide), and metal amides (e.g., lithium hexamethyldisilazide). Suitable solvents include alcohols (e.g., methanol, ethanol), amides (e.g., dimethylformamide, dimethylacetamide, N-methylpyrrolidone), ethers (e.g., tetrahydrofuran, dioxane, dimethoxyethane), and nitriles (e.g., acetonitrile).

Any suitable amount of solvent may be used. In one embodiment, the amount is from about 1 to about 50, about 5 to about 30, or about 10 to about 25 times the weight amounts of the starting compound. Similarly, the any suitable amount of base may be used. In one embodiment, the amount is from about 1 to about 10, about 1 to about 5, or about 1 to about 3 molar equivalents of the starting compound.

Any suitable amount of cyanoacetamide may be used. In one embodiment, the amount is from about 1 to about 5, from about 1 to about 3, or from about 1 to about 2 molar equivalents of the starting compound. The cyanoacetamide may be dissolved, dispersed, suspended or otherwise suitably distributed in the solvent. Preferably, the base is then added to the mixture, which is maintained at a suitable temperature (e.g., from about −10° C. to about 60° C., about −10° C. to about 40° C., or about 10° C. to about 30° C.) for an amount of time sufficient for the reaction to occur (e.g., from about 0 to about 5 hours, about 0.25 to about 5 hours, or about 0.25 to about 1 hours).

The compound of formula III may be dissolved, dispersed, suspended or otherwise suitably distributed in the reaction mixture. In a particular embodiment, it is added over a time of from about 0 to about 5 hours, about 0.25 to about 5 hours, or about 0.25 to about 2 hour. The mixture may be stirred or otherwise suitably mixed to facilitate the reaction. The reaction itself may be conducted at any suitable temperature (e.g., from about 0° C. to about 100° C., about 20° C. to about 80° C., or about 40° C. to about 60° C.) or an amount of time sufficient for it to occur (e.g., from about 0.5 to about 20 hours, about 0.5 to about 10 hours, or about 1 to about 5 hours).

A specific method of the invention is represented below:

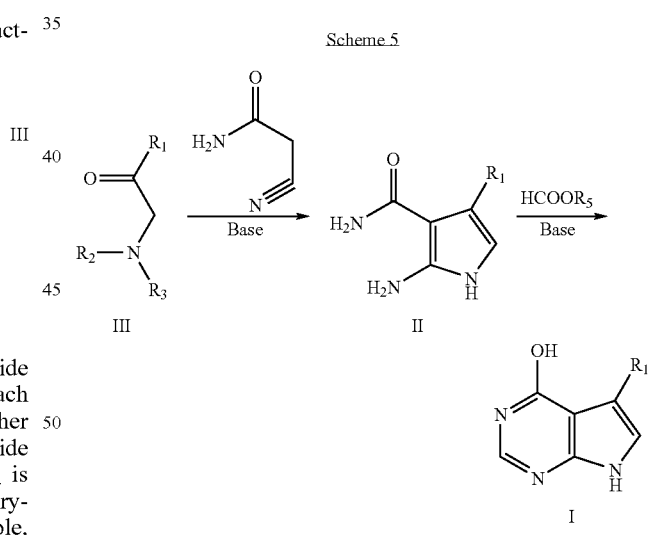

Scheme 5

In this method, the use of a mononitrile (cyanoacetamide), instead of a symmetrical dinitrile (e.g., malonitrile), provides compounds of formula II in good yield. In one embodiment, the compound of formula II is isolated. In another, it is not.

5. EXAMPLES

Aspects of this invention can be understood from the following examples, which do not limit its scope.

Reagents and solvents were obtained from commercial sources and used as received. All solvents used were of HPLC grade. NMR spectra were recorded with a Bruker ARX 300, Bruker DPX 400 or Varian Mercury 400. HPLC analysis was performed on a Shimadzu instrument with a PDA detector. HPLC/MS analysis was carried out on a Waters ZQ or Shimadzu instrument.

5.1. Example 1

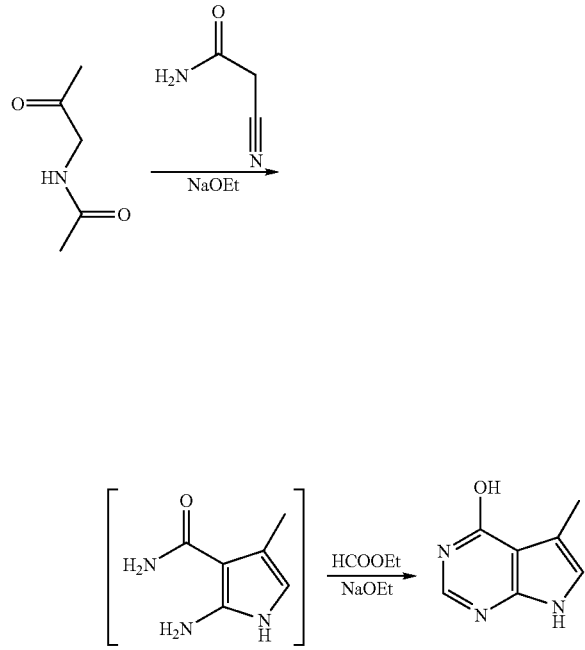

To a solution of cyanoacetamide (14.0 g, 1.08 eq) in ethanol (175 ml) was added 21% sodium ethoxide solution in ethanol (198.8 g, 3.99 eq) at room temperature. To the resulting mixture was added acetamidoacetone (17.7 g, 154 mmol, prepared according to Wiley and Borum, *J. Am. Chem. Soc.* 70:2005 (1948)). The resulting mixture was then heated at 50° C. for 3.25 h. HPLC analysis of the reaction mixture indicated that the pyrrole compound was formed in about 67% of the HPLC area. An analytical sample of the pyrrole compound was isolated by aqueous work-up followed by purification with column chromatography. MS: $MH^+$=140.1. $^1$H NMR (DMSO-$d_6$): δ 9.71 (br s, 1H), 6.08 (br s, 2H), 5.84 (s, 1H), 5.64 (s, 2H), 2.07 (s, 3H); $^{13}$C NMR (DMSO-$d_6$): δ 169.2, 146.7, 113.8, 108.0, 95.5, 13.4.

Without isolation, to the above pyrrole reaction mixture was added ethyl formate (40 ml, 3.22 eq) at 50° C. After about 3.5 h heating at 50° C., the reaction mixture was concentrated under vacuum. The residue was dissolved in water (200 ml) at 40-45° C. The pH of the solution was adjusted to about 5.6 using 6 N HCl. The solution was concentrated at 65-70° C. under vacuum to about 200 ml and the resulting suspension was cooled slowly to room temperature. The solids were filtered, washed with water, and dried at 55° C. under vacuum to give the final product as a red powder (8.14 g, 36% yield, purity: 98.0% by HPLC area). MS: $MH^+$=150.1. $^1$H NMR (DMSO-$d_6$): δ 2.27 (s, 3H), 6.74 (s, 1H), 7.74 (s, 1H), 11.53 (br s, 2H). $^{13}$C NMR (DMSO-$d_6$): δ 11.6, 107.0, 113.8, 117.8, 143.5, 148.2, 159.6.

5.2. Example 2

A mixture of cyanoacetamide (8.8 g, 1.5 eq) and lithium hydroxide powder (2.5 g, 1.5 eq) was dissolved in methanol (100 ml) and the resulting solution was stirred at room temperature for 30 min. To this solution was added acetamidoacetone (8.0 g, 60 mmol) and the resulting mixture was stirred at room temperature for 2 h. To this mixture was added 25% sodium methoxide (24 ml, 1.5 eq) and the resulting mixture was heated at 60° C. for 2 h. HPLC/MS analysis of the red reaction mixture indicated that formation of 2-amino-4-methyl-1H-pyrrole-3-carboxamide was essentially complete. To this reaction mixture was added ethyl formate (28 ml, 5.0 eq) in one portion followed by 25% sodium methoxide (48 ml, 3 eq) at 50-60° C. over 30 min. After about 7 h heating at 60° C., water (30 ml) was added and the mixture was heated at 60° C. for 30 min. HPLC analysis showed that the final product was formed in 73% solution yield. Solvent was removed under vacuum and the concentrated mixture was diluted with water to about 200 ml volume. The pH of the solution was adjusted to about 7.5 using 6 N HCl at room temperature. The solids were filtered, washed with water, and dried at 50° C. under vacuum to give the final compound as a purple powder (6.0 g, 58% yield, purity: 100% by HPLC area).

5.3. Example 3

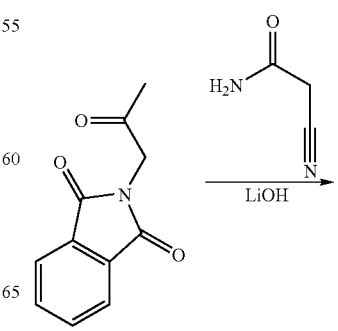

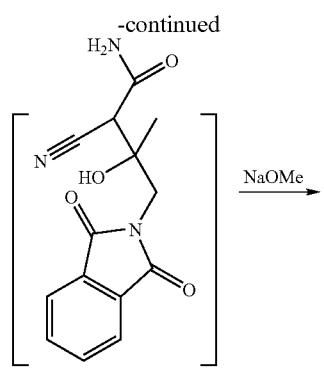

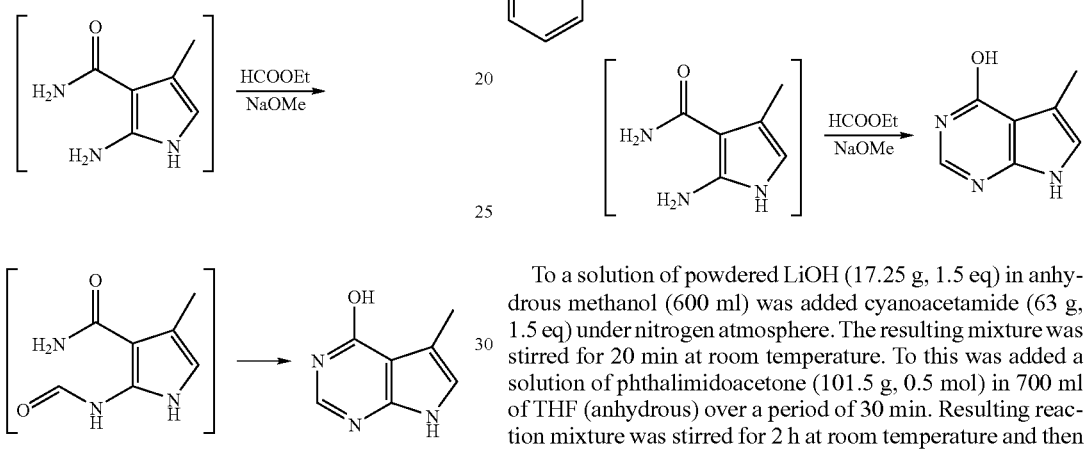

Cyanoacetamide (62 g, 1.5 eq) and powdered lithium hydroxide (18 g, 1.5 eq) were mixed in 500 ml DMF and it was stirred at room temperature for 30 min. To the mixture was added a solution of phthalimidoacetone (100 g, 0.49 mol, purchased from TCI America, Portland, Oreg., USA, or prepared according to Lei, et al, *J. Am. Chem. Soc.* 2004, 126, 1626) in DMF (200 ml) over 1 h at room temperature. Additional DMF (25 ml) was used as a rinse. After stirring at room temperature for 5 min, HPLC/MS showed formation of the adol compound (MS: $MH^+=222.1$, $MNa^+=244.0$). Methanol (50 ml) was added followed by 25% sodium methoxide solution (160 g, 1.5 eq) and methanol rinse (50 ml). This mixture was heated at 60-65° C. for 2 h to form 2-amino-4-methyl-1H-pyrrole-3-carboxamide. To this reaction mixture was added ethyl formate (100 ml, 2.5 eq) at 40-60° C. After stirring for 15 min, more methanol (50 ml) was added followed by simultaneous addition of ethyl formate (100 ml, 2.5 eq) and 25% sodium methoxide solution (266 g, 2.5 eq) over 30 min. Additional methanol (50 ml) was added as rinse. The resulting mixture was heated at 60° C. for 5 h. More 25% sodium methoxide solution (113 ml, 1 eq) was added, and heating continued for 1 h more to convert all of the pyrrole N-formyl intermediate (MS: $MH^+=151.1$). Water (400 ml) was added and mixture was heated at 60° C. for 30 min. Solution assay indicated the final product was formed in 69% yield. The hydrolyzed reaction mixture was concentrated under vacuum and diluted with water (1000 ml). The pH was adjusted to about 7.6 with 6 N HCl at 60-65° C. The resulting slurry was heated at 60-65° C. for 15 min and cooled slowly to 10° C. The solids were filtered, washed with water, and dried at 50-60° C. under vacuum. The final product was obtained as a light purple solid (39.5 g, 54% yield, purity: 99.8% by HPLC area).

5.4. Example 4

To a solution of powdered LiOH (17.25 g, 1.5 eq) in anhydrous methanol (600 ml) was added cyanoacetamide (63 g, 1.5 eq) under nitrogen atmosphere. The resulting mixture was stirred for 20 min at room temperature. To this was added a solution of phthalimidoacetone (101.5 g, 0.5 mol) in 700 ml of THF (anhydrous) over a period of 30 min. Resulting reaction mixture was stirred for 2 h at room temperature and then heated at 55° C. for 1 h. To this was added sodium methoxide solution (25% solution, 172 ml, 1.5 eq) at 55° C. over a period of 40 min. After 3 h HPLC/MS indicated starting material and intermediates were converted to 2-amino-4-methyl-1H-pyrrole-3-carboxamide. To this reaction mixture was added ethyl formate (200.8 ml, 5 eq) over a period of 20 min followed by sodium methoxide (25% solution, 324 g, 3 eq). The resulting reaction mixture was heated for 7 h at 55° C. at which time HPLC/MS indicated that the intermediate pyrrole compound was converted to the final product. The reaction mixture was diluted with 1.5 L water, heated at 60° C. for 1 h, and then concentrated to small volume (11.5 L). Solution assay indicated that final product was formed in 75% solution yield. This solution was acidified to pH 7.5 with 6 N aq. HCl, cooled to about 5° C., and held at this temperature for 30 min. The solid was filtered, washed with water, dried at 50° C. under vacuum overnight to give the final product as a light brown solid (45.8 g, 61% yield, purity: 99.0% by HPLC area).

5.5. Examples 5-13

Similar to Examples 3 and 4,5-methyl-7H-pyrrolo[2,3-d]pyrimidin-4-ol was prepared using the following solvent/base combinations for the preparation of the 2-amino-4-methyl-1H-pyrrole-3-carboxamide intermediate:

| Example | Base | Solvent | Solution Yield | Isolated Yield | HPLC Purity |
|---|---|---|---|---|---|
| 5 | 25% $NaOCH_3$ (1.8eq) | MeOH | 63% | 53% | 100% |
| 6 | 25% $NaOCH_3$ (1.5eq) | DMF/MeOH | 55% | 45% | 99.8% |

-continued

| Example | Base | Solvent | Solution Yield | Isolated Yield | HPLC Purity |
|---|---|---|---|---|---|
| 7 | LiOH (1.5eq) | MeOH | 54% | Not isolated | — |
| 8 | a. NaOH (1.5eq)<br>b. 25% NaOCH₃ (1.5eq) | DMF/<br>MeOH | 74% | 58% | 100% |
| 9 | a. NaOH (1.5eq)<br>b. 25% NaOCH₃ (1.5eq) | MeOH | 60% | 50% | 100% |
| 10 | LiOMe (1.4eq) | DMF/<br>MeOH | 58% | Not isolated | — |
| 11 | a. LiOH (0.5eq)<br>b. 25% NaOCH₃ (2eq) | DMF/<br>MeOH | 65% | Not isolated | — |
| 12 | a. LiOH (1.2eq)<br>b. 25% NaOCH₃ (2eq) | DMF/<br>MeOH | 69% | 58% | 100% |
| 13 | a. LiOH (2eq)<br>b. 25% NaOCH₃ (2eq) | DMF/<br>MeOH | 62% | 48% | 100% |

All references (e.g., patents and patent applications) cited herein are incorporated herein by reference in their entireties.

What is claimed is:

1. A method of preparing a compound of formula I:

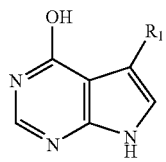

I or a salt thereof, which comprises contacting a compound of formula II:

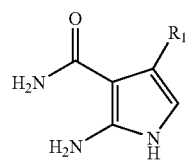

II with a compound of formula HCOOR₅ under basic conditions sufficient to provide the compound of formula I, wherein:
  $R_1$ is hydrogen or optionally substituted alkyl, aryl, heterocycle, arylalkyl, or heterocycloalkyl; and
  $R_5$ is optionally substituted alkyl, aryl, or arylalkyl.

2. The method of claim 1, wherein the compound of formula II is prepared by contacting a compound of formula III:

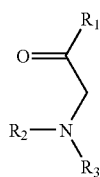

III with cyanoacetamide under conditions sufficient to provide the compound of formula II, wherein:

$R_2$ and $R_3$ are each independently hydrogen or $R_4CO—$, or are taken together with the nitrogen atom to which they are attached to provide a heterocycle; and
$R_4$ is optionally substituted alkyl, aryl, arylalkyl, alkoxy, or aryloxy.

3. The method of claim 1, wherein the basic conditions are afforded by a base in a solvent.

4. The method of claim 3, wherein the base is a metal hydroxide, metal alkoxide, metal amide, or mixture thereof.

5. The method of claim 4, wherein the metal hydroxide is lithium hydroxide, sodium hydroxide, or potassium hydroxide.

6. The method of claim 4, wherein the metal alkoxide is lithium methoxide, sodium methoxide, or sodium ethoxide.

7. The method of claim 4, wherein the metal amide is lithium hexamethyldisilazide.

8. The method of claim 3, wherein the solvent is an alcohol, amide, ether, nitrile, or mixture thereof.

9. The method of claim 8, wherein the alcohol is methanol or ethanol.

10. The method of claim 8, wherein the amide is dimethylformamide, dimethylacetamide, or N-methylpyrrolidone.

11. The method of claim 8, wherein the ether is tetrahydrofuran, dioxane, or dimethoxyethane.

12. The method of claim 8, wherein the nitrile is acetonitrile.

13. The method of claim 8, wherein the solvent comprises methanol and dimethylformamide.

14. The method of claim 2, wherein the conditions sufficient to provide the compound of formula II comprise a base in a solvent.

15. The method of claim 14, wherein the base is a metal hydroxide, metal alkoxide, metal amide, or mixture thereof.

16. The method of claim 15, wherein the metal hydroxide is lithium hydroxide, sodium hydroxide, or potassium hydroxide.

17. The method of claim 15, wherein the metal alkoxide is lithium methoxide, sodium methoxide, or sodium ethoxide.

18. The method of claim 15, wherein the metal amide is lithium hexamethyldisilazide.

19. The method of claim 14, wherein the solvent is an alcohol, amide, ether, nitrile, or mixture thereof.

20. The method of claim 19, wherein the alcohol is methanol or ethanol.

21. The method of claim 19, wherein the amide is dimethylformamide, dimethylacetamide, or N-methylpyrrolidone.

22. The method of claim 19, wherein the ether is tetrahydrofuran, dioxane, or dimethoxyethane.

23. The method of claim 19, wherein the nitrile is acetonitrile.

24. The method of claim 19, wherein the solvent comprises methanol and dimethylformamide.

25. The method of claim 1, wherein $R_1$ is hydrogen.

26. The method of claim 1, wherein $R_1$ is lower alkyl.

27. The method of claim 2, wherein $R_2$ is hydrogen.

28. The method of claim 2, wherein $R_3$ is $R_4CO—$.

29. The method of claim 28, wherein $R_4$ is alkyl or aryl.

30. The method of claim 2, wherein $R_2$ and $R_3$ taken together with the nitrogen atom to which they are attached form phthalimido or succinimido.

31. The method of claim 1, wherein $R_5$ is lower alkyl or phenyl.

32. The method of claim 31, wherein $R_5$ is ethyl.

* * * * *